United States Patent [19]

Stevens

[11] Patent Number: 4,820,259
[45] Date of Patent: Apr. 11, 1989

[54] EXTERNAL EAR CLEANING DEVICE

[76] Inventor: Robert B. Stevens, P.O. Box 36222, Grosse Pointe, Mich. 48236

[21] Appl. No.: 55,950

[22] Filed: Jun. 1, 1987

[51] Int. Cl.⁴ ............................................ A61M 35/00
[52] U.S. Cl. ............................................ 604/2; 604/1
[58] Field of Search ................ 604/1, 2, 3; 128/67, 128/756

[56] References Cited

U.S. PATENT DOCUMENTS

| | | | |
|---|---|---|---|
| 2,510,961 | 6/1950 | Davis | 604/1 |
| 2,876,501 | 3/1959 | Glickston | 604/1 X |
| 3,586,380 | 6/1971 | Allbeckoff | 604/1 X |

Primary Examiner—Allen M. Ostrager
Attorney, Agent, or Firm—Hurt, Richardson, Garner, Todd & Cadenhead

[57] ABSTRACT

An external ear cleaning device which is specially adapted for reaching the surfaces of the curved portions of the external ear. A substantially inflexible shaft has attached thereon at least one end piece constructed of a flexible material capable of absorbing water. The flexible material is deformable when pressure is applied to the shaft, such that the end piece can contact normally inaccessible portions of the external ear. The end piece also has a portion which extends radially outward from the shaft and which prevents harmful insertion of the device into the ear opening.

9 Claims, 2 Drawing Sheets

EXTERNAL EAR CLEANING DEVICE

BACKGROUND OF THE INVENTION

The present invention relates to a device for cleaning the external portions of the ear, including the normally difficult to clean curved portions of the ear. In addition, the possibility of inserting the device into the ear opening is reduced or eliminated due to the unique construction of the device. The device is designed to be used when wetted, as for example, when used in a bath or shower.

The structure of the outer ear of humans and certain primates is designed to enhance the capture of sound and to offer protection for the internal portions of the ear. For these purposes, the external ear has a plurality of curved portions. Unfortunately, these curved portions also provide ideal locations for the collection of dirt. This collection process is enhanced in some individuals due to excessive secretion of skin oil which binds with the dirt. Devices of the prior art which could be used to remove the accumulated dirt have generally proved unsatisfactory. Complete removal of the dirt accumulations, as with the removal of dirt from other portions of the body, generally requires the use of soap and water. Hand washing of the ear with wash cloths is oftentimes unsatisfactory because all of the intricate surfaces in the ear cannot be reached. Moreover, because the wash cloth is normally much larger than is actually needed for cleaning of the ear, those portions of the cloth not being used present a possible source of soap and/or water which can enter the ear opening, causing irritation or damage to the ear.

The commonly used cotton swabs, which consist of a ball of cotton on each end of a fiber shaft, are not designed for use in wet environments. When wetted, the cotton end pieces unravel, and their effectiveness in the removal of accumulated dirt thereby drastically decreases. Moreover, such cotton swabs generally are incapable of retaining sufficient amounts of soap or other cleaning material so as to be effective in cleaning without the addition of cleaning material from another source. Thus, even if cotton swabs were effective when wet, the inconvenience of the need for an external supply of soap makes the swabs relatively undesirable in this application. The fiber shafts of the prior art cotton swabs also are easily bent, especially when wetted. To adequately clean the external ear, substantial pressure must oftentimes be applied to the shaft by the user, resulting in bending or breakage of the shaft, and thereby inadequate cleaning.

A further disadvantage of cotton swabs is the possibility that the swab may be accidentally inserted into the ear opening, causing damage to the ear canal, ear drum, etc. Since cotton swabs can lose their integrity when wet, as noted above, the accidental insertion of a swab into the ear opening could result in the retention of cotton fibers in the ear, which could be a source of infection.

U.S. Pat. No. 2,490,168 relates to an applicator for sinus medication. As set forth in column 1, lines 7-18, the applicator has at its forward end an absorbent external ply capable of holding and delivering medication. The applicator has a degree of rigidity such that "it may be propelled through [sinus] passages". The head is preferably a porous or spongy body, sponge rubber being preferred. The form of the head is preferably that of a teardrop.

U.S. Pat. No. 3,923,061 relates to a padding comprising flexible laminations connected to a stick. The padding can be manufactured of rubber or plastic. The device can be used for the deposit of "pasty or liquid substances in great quantities, which will have been previously inserted between the laminations".

U.S. Pat. No. 3,626,946 relates to an ear cleaning device which includes a non-woven fabric twisted and pressed about cigar-shaped mandrel for insertion into the human ear.

U.S. Pat. No. 4,259,955 relates to a swab formed of an elongated support having knot terry piles mounted thereon to form a head.

None of the above-described prior art devices, however, can adequately remove accumulated dirt from the various portions of the external ear, due to the lack of proper shape of the cleaning portion, or to the use of inadequate materials of construction.

DISCLOSURE OF THE INVENTION

It is accordingly an object of the invention to provide a device for cleaning the external ear, which is capable of removing accumulated dirt from relatively inaccessible curved portions of the ear.

It is another object of the invention to provide a device, as above, which is usable when wet, and which retains its integrity when so used.

It is yet another object of the invention to provide a device, as above, which reduces or eliminates the possibility of accidental insertion into the ear opening.

It is still another object of the invention to provide a device, as above, which is capable of retaining a quantity of cleaning material which is released when the device is wetted.

These objects are achieved by a device for cleaning an external ear surrounding an ear opening and further having a plurality of curved portions, the device comprising a substantially inflexible shaft, and a moisture absorbent end piece positioned over at least one end of the inflexible shaft, the end piece including a first portion attached on a first side to the end of the shaft and having a first outer circumference, and a second portion attached to the first portion on a second side opposite the first side and extending outward from the first portion, the second portion having a second outer circumference smaller than the first outer circumference, wherein at least the first portion of the end piece has at least one cross-sectional dimension larger than the diameter of the ear opening to prevent insertion of the first portion into the ear opening, and wherein at least the second portion of the end piece is engageable with the surface of the curved portions of the external ear for cleaning the curved portions.

BRIEF DESCRIPTION OF THE DRAWINGS

For a clear understanding of the true scope of the invention, the following detailed description should be read in conjunction with the drawings, wherein.

DETAILED DESCRIPTION OF THE PREFERRED EMBODIMENTS

Figure 1A:
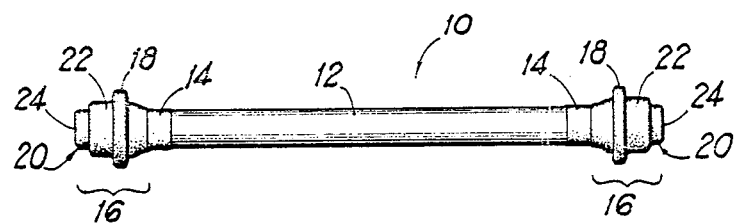
FIG. 1A is a side view of one embodiment of the invention in its dry state.
Figure 1B:
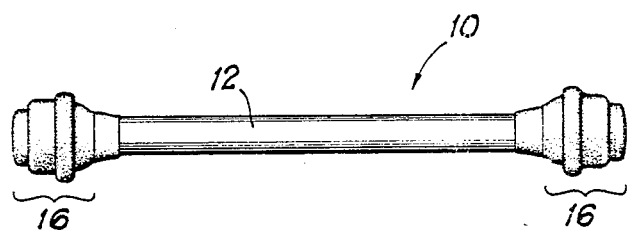
FIG. 1B is a side view of the same embodiment of the invention in a swollen state caused by wetting.

FIGS. 1A and 1B illustrate one embodiment of the invention, which is generally indicated by the number 10. The device 10 comprises a substantially inflexible shaft 12 having at each end 14 a moisture absorbent end piece 16.

The device 10 is preferably constructed of a single piece moisture absorbent material which can be cut from a block of the material or molded, using well known techniques. The end pieces preferably have a cleaning agent, such as soap, incorporated therein.

Suitable materials for the device 10 include the various synthetic sponges made from polymers such as polyester. In general, materials suitable for use in the device 10 are those having the ability to absorb moisture to an extent sufficient to wet the cleaning agent contained in the material.

The shaft is treated with a stiffening agent so that it does not bend substantially upon application of pressure applied by the user in cleaning of the ear. In addition, the shaft is preferably waterproofed. The waterproofing and stiffening can be provided by a chemical such as HiLoft 6279, manufactured by National Starch and Chemical Corporation. This chemical is a self reactive, vinyl acetate terpolymer emulsion.

In contrast to the shaft, the end pieces 16 are left untreated with the stiffening agent, and thus, especially upon wetting, are relatively flexible. The shape of the end piece is important from the standpoint of reaching all of the surfaces formed by the curved portions of the external ear.

Again with reference to FIG. 1A, the moisture absorbent end pieces 16 comprise a first portion 18 which is attached to the end 14 of the shaft 12. Secured on top of the first portion 18 is a second portion 20 which can comprise a first cylindrical section 22 and a second cylindrical section 24. The circumference of each cylindrical section 22 and 24 is less than that of the first portion 18, with section 24 having a smaller circumference than section 22. By providing progressively smaller circumferences for the two cylindrical sections 22 and 24, insertion of the end piece 16 into the curved portions of the external ear is facilitated.

FIG. 1B illustrates qualitatively the expansion of the end pieces 16 when the device of the invention is wetted. Generally, the expansion is from about 5 to about 30% of the original volume of the end pieces depending on the construction material and manufacturing process. The shaft 12 generally does not expand due to the impregnation of the stiffening agent.

Figure 3A:
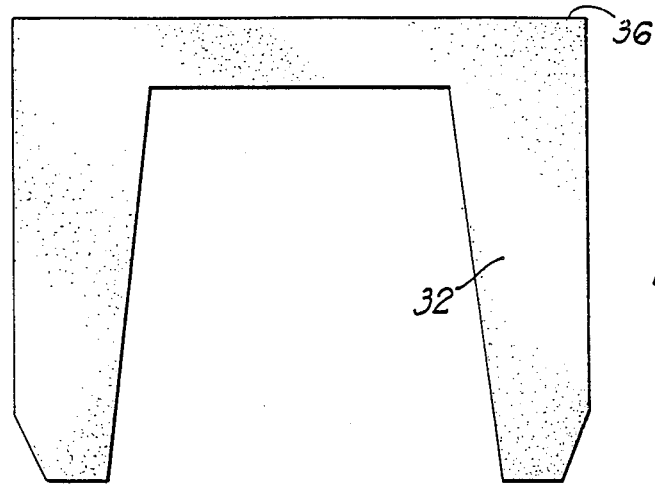
FIGS. 3A through 3D illustrate various stages in the construction of a second embodiment of the invention, in which successive sections of absorbent sheets are rolled together.
Figure 3B:
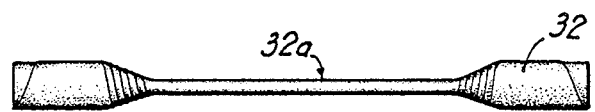
Figure 3C:
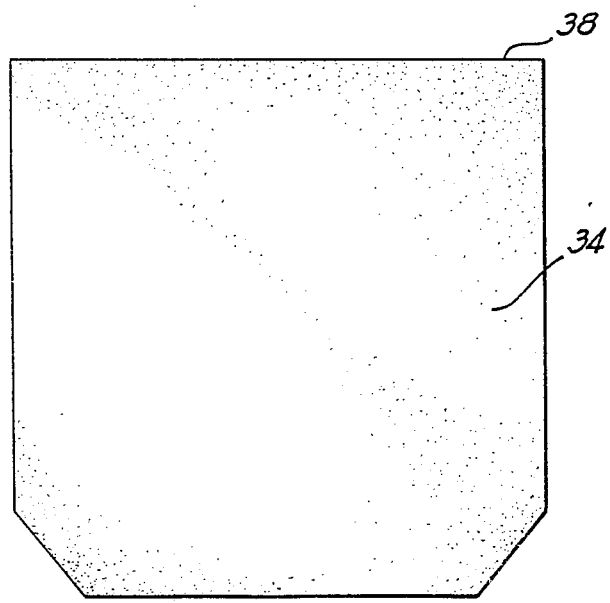
Figure 3D:
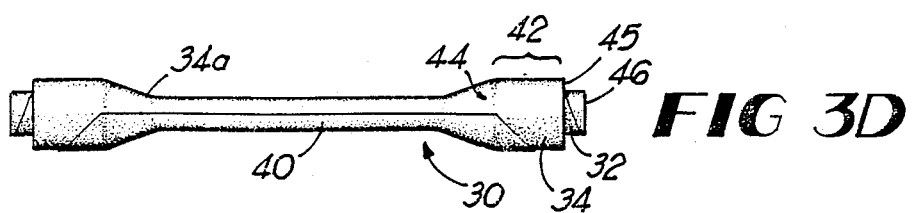

FIGS. 3A through 3D illustrate a second embodiment of the invention which is indicated generally by the number 30. The ear cleaning device 30 is prepared by rolling together one or more absorbent sheets 32 and 34. The absorbent sheets are preferably non-woven fibers, for example, any of the various foamed polymer materials used in the art. Examples include polyurethane, polyethylene, polyvinyl chloride and various well known copolymers thereof. Other foamed copolymers can be used which provide equivalent performance. To produce the ear cleaning device 30, the absorbent sheet 32, which is generally in the form of a "U", is first rolled upon itself beginning at the end 36. The resulting rolled structure 32a is illustrated in FIG. 3B. Sheet 34 is then rolled around rolled sheet 32 beginning at end 38. The finished result is ear cleaning device 30 as shown in FIG. 3D having rolled sheet 34, and rolled sheet 32a extending outwardly from sheet 34. As with the first embodiment 10 of the invention, ear cleaning device 30 has a shaft portion 40 and end pieces 42 which, being integral with the shaft, are "attached" to the latter at shaft ends 44. In the manufaturing process, a single or multiple sheet process may be used to achieve a function tip and shaped shaft.

Also as with the first embodiment, the shaft 40 of ear cleaning device 30 is substantially rigid. The rigidity can be effected by, for example, compressing the shaft and treating it with a chemical binder, by wrapping the shaft with thread or wire, or by positioning a reinforcing element within the shaft, such as a rod or tube (not shown) made of, for example, metal or cardboard.

The end pieces 42 can be coated with a cleaning agent, such as soap. Each end piece includes a first portion 45, formed by the end of the second rolled absorbent sheet 34a, and a second portion 46 formed by the end of the first rolled absorbent sheet 32a, the rolled sheet 32a extending from rolled sheet 34a, as shown in FIG. 3D.

Figure 2:
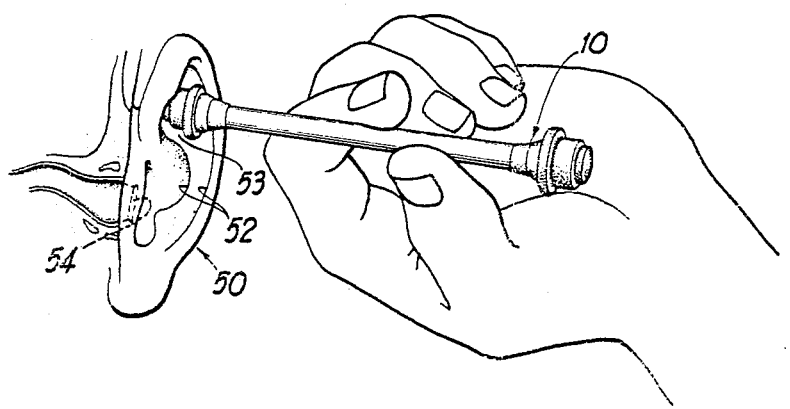
FIG. 2 illustrates use of the device of the invention in the cleaning of the external ear.

The use of the device is illustrated in FIG. 2, where an external ear, indicated generally by the number 50, contains a plurality of curved portions 52 and surfaces 53, and an ear opening 54. The ear cleaning device 10 or 30 is inserted into the curved portions of the external ear to clean the normally hard to reach surfaces 53. The second portion 20 or 46 is particularly adapted to reach into all areas of the external ear due to its smaller size compared to the first portion 18 or 44, respectively.

The first portions 18 or 44 preferably are circular in cross-section, but may be oval-shaped, square, etc., the only critical requirement being that at least one cross-sectional dimension of the first portion 18 or 44 must be greater than the diameter of the ear opening 54. Such a construction thereby prevents the end piece from being inserted into the ear opening 54 to an extent beyond the second portion 20 or 46.

Because the surfaces 53 of the curved portions of the external ear are in some places extremely difficult to reach, considerable pressure must be exerted by the user on the shaft 12 or 40 so that the end piece 16, 42 is partially compressed and thereby conformed to the surface 53. Because the shaft is substantially inflexible, such pressure can be applied without the shaft bending to a considerable extent and possibly breaking.

Since the end pieces are formed of a sponge-like material, which retains its integrity when wet, there is no danger of disintegration of the end pieces when inserted into the external ear, as is the case with cotton swabs. Further, because of the use of a sponge material, a cleaning agent, such as soap, can readily be incorporated into the end pieces and retained therein until the device is wetted.

With regard to specific dimensions of the ear cleaning device of the invention, the following are illustrative. The shaft length is from about 2 to about 5 inches, with from about 3 to about 4 inches preferred. The shaft diameter is from about ⅛ to about ½ inch, with from about ¼ to about 5/16 inch preferred. The first portion 18, 44 has a length of from about ¼ to about ¾ inch, with from about ¼ to about ½ inch preferred, while the diameter of the first portion can vary from about ¼ to about ¾ inch, with from about ⅜ to about ½ inch preferred. The cylindrical section 22 has a length of from about ⅛ to about ⅜ inch, with from about ⅛ to about ¼ inch preferred. The cylindrical section 24 has a length of from about ⅛ inch to about ¼ inch with from about ⅛ inch to about 3/16 inch preferred. The diameter of the cylindrical section 22 can vary from about ⅛ inch to about ½ inch with from about ¼ to about ⅜ inch preferred. The diameter of the cylindrical section 24 can vary from about 1/16 inch to about ⅜ inch, with from about ⅛ to about ¼ inch preferred.

The particular dimensions can vary depending on the use. For example, the device of the invention can be tailored for use with an infant, young child, or adult, the dimensions being adjusted accordingly. A device used for cleaning the ears of infants may have a first portion with a diameter of ¼ inch, which would be sufficient to prevent insertion into the infant ear opening.

The invention has been described in detail with particular reference to preferred embodiments thereof but it will be understood that variations and modifications can be effected within the spirit and scope of the invention as described hereinabove and as defined in the appended claims.

What is claimed is:

1. A generally dowel-shaped device for cleaning an external ear having an ear opening and further having a plurality of curved portions which define surfaces, the device comprising:
    a substantially inflexible shaft;
    a moisture absorbent end piece positioned over at least one end of said shaft, said end piece including:
    a first portion attached to said end of said shaft and having a first outer circumference;
    a second portion attached to said first portion on a side opposite said shaft and extending outward from said first portion and said shaft, said second portion having a second outer circumference smaller than said first outer circumference;
    wherein said first portion of said end piece has at least one cross-sectional dimension larger than the diameter of the ear opening to prevent insertion of said first portion into said ear opening, and wherein at least said second portion of said end piece is engageable with both the outer surface portion of the auditory canal and the surfaces of the curved portions of the external ear for cleaning said surfaces.

2. A device as claimed in claim 1, wherein a separate said moisture absorbent end piece is positioned on each end of said shaft.

3. A device as claimed in claim 1, wherein said moisture absorbent end piece contains a cleaning substance.

4. A device as claimed in claim 1, wherein said shaft and said moisture absorbent end piece comprise a single piece of synthetic sponge, said shaft including stiffening means.

5. A device as claimed in claim 1, wherein said inflexible shaft has a longitudinal axis, and wherein said first portion comprises an annulus attached to said end of said shaft, the outer circumference of said annulus lying in a plane substantially perpendicular to said longitudinal axis.

6. A device as claimed in claim 5, wherein said second portion extends from said first portion in a direction parallel to said longitudinal axis, said second portion including a first cylindrical section attached to said first portion on a first side and a second cylindrical section attached to said first cylindrical section on a second side opposite said first side, said second cylindrical section having a smaller diameter than said first cylindrical section.

7. A device as claimed in claim 1, wherein said device comprises a rolled material forming said shaft and said end piece, said shaft including stiffening means.

8. A device as claimed in claim 7, wherein said rolled material is a synthetic non-woven material.

9. A device as claimed in claim 1, wherein said moisture absorbent end piece is expandable upon wetting.

* * * * *